(12) United States Patent
Zoughi et al.

(10) Patent No.: US 9,482,627 B2
(45) Date of Patent: Nov. 1, 2016

(54) TIRE INSPECTION USING MICROWAVE IMAGING METHODOLOGIES

(71) Applicants: Compagnie Generale des Etablissements Michelin, Clermont-Ferrand (FR); Michelin Recherche et Technique S.A., Granges-Paccot (CH)

(72) Inventors: Reza Zoughi, Wildwood, MO (US); Mohammad Tayeb Ghasr, Rolla, MO (US)

(73) Assignees: Michelin Recherche et Technique S.A., Granges-Paccot (CH); Compagne Generale des Etablissements Michelin, Clermont-Ferrand (FR)

( * ) Notice: Subject to any disclaimer, the term of this patent is extended or adjusted under 35 U.S.C. 154(b) by 346 days.

(21) Appl. No.: 14/444,851

(22) Filed: Jul. 28, 2014

(65) Prior Publication Data
US 2015/0035547 A1 Feb. 5, 2015

Related U.S. Application Data

(60) Provisional application No. 61/860,891, filed on Jul. 31, 2013.

(51) Int. Cl.
| | | |
|---|---|---|
| G01R 27/04 | (2006.01) | |
| G01R 27/32 | (2006.01) | |
| G01N 22/02 | (2006.01) | |
| B29D 30/00 | (2006.01) | |
| G01N 22/00 | (2006.01) | |
| G01R 27/28 | (2006.01) | |
| G01R 27/06 | (2006.01) | |
| G01M 17/02 | (2006.01) | |
| G01R 31/11 | (2006.01) | |

(52) U.S. Cl.
CPC ......... *G01N 22/02* (2013.01); *B29D 30/0061* (2013.01); *G01M 17/025* (2013.01); *G01N 22/00* (2013.01); *G01R 27/06* (2013.01); *G01R 27/28* (2013.01); *B29D 2030/0066* (2013.01); *G01R 31/11* (2013.01)

(58) Field of Classification Search
CPC ...... G01R 27/28; G01R 27/06; G01R 31/11; G01N 22/00
USPC .................. 324/76, 459, 600, 629, 637–648; 342/165
See application file for complete search history.

(56) References Cited

U.S. PATENT DOCUMENTS

| | | | | |
|---|---|---|---|---|
| 6,005,397 A | * | 12/1999 | Zoughi | ................. G01B 15/02 324/644 |
| 2010/0283483 A1 | * | 11/2010 | Little, Jr. | ............... G01N 22/00 324/642 |
| 2012/0037804 A1 | * | 2/2012 | Federici | ............. G01N 21/3586 250/341.1 |

*Primary Examiner* — Jermele M Hollington
*Assistant Examiner* — Raul Rios Russo
(74) *Attorney, Agent, or Firm* — Neal P. Pierotti

(57) ABSTRACT

A method of inspection of a tire was developed using microwave imaging comprising the steps of selecting a plurality of regions from within a tire to be imaged; determining the dielectric properties of the tire components in each of the selected regions in a plurality of frequency bands; selecting a specific location on a tire to be imaged; providing a scanning platform for microwave imaging of the tire; imaging the selected location on a tire using microwave imaging at a plurality of microwave scanning frequencies and at a selected microwave polarization to obtain images of the internal state of the sample; and filtering the images to remove the effects of curvature of the selected location of the tire.

13 Claims, 13 Drawing Sheets

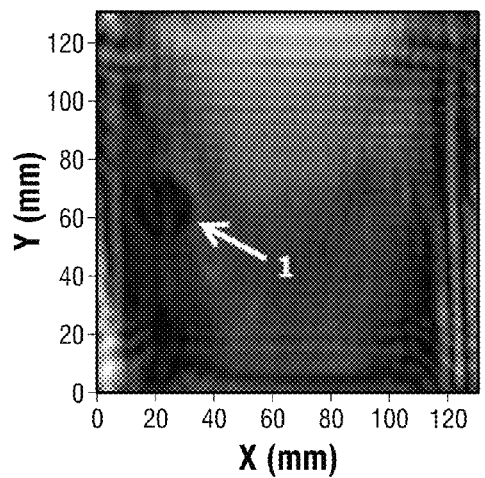
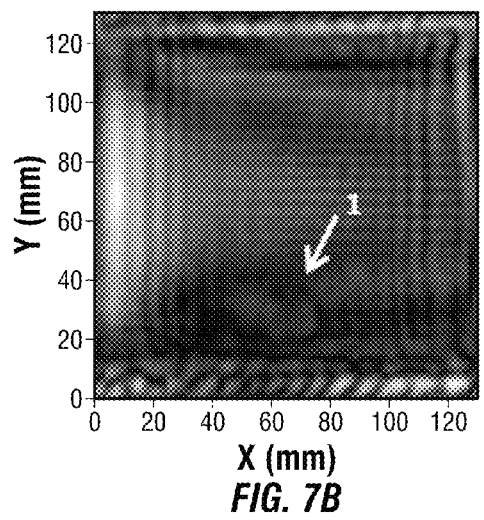
FIG. 7A  FIG. 7B
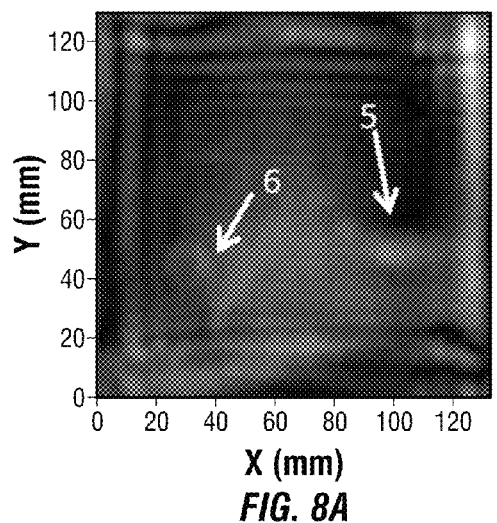
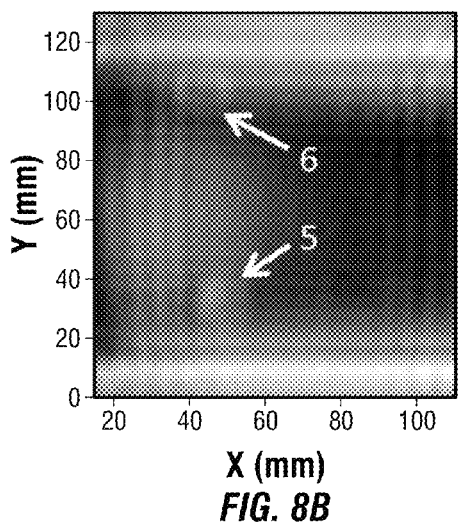
FIG. 8A  FIG. 8B

PERPENDICULAR TO WIRES

PARALLEL TO WIRES

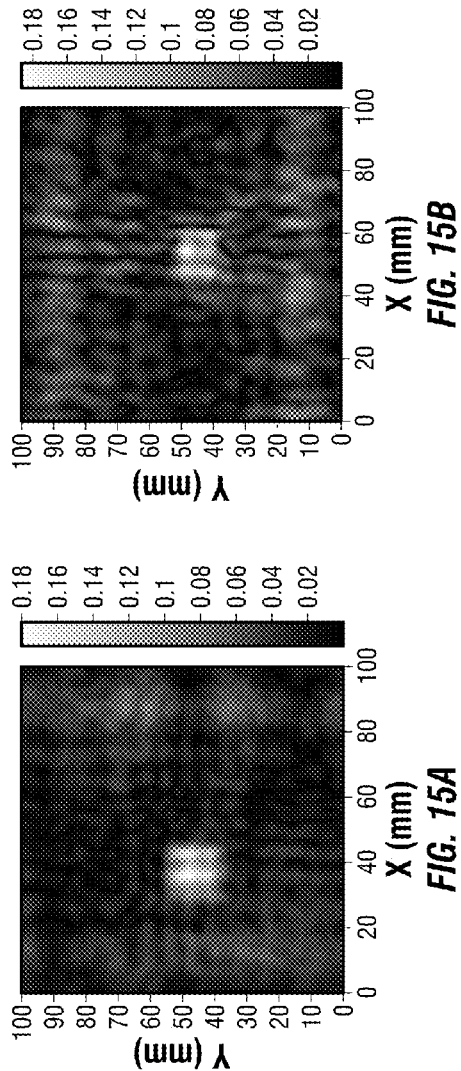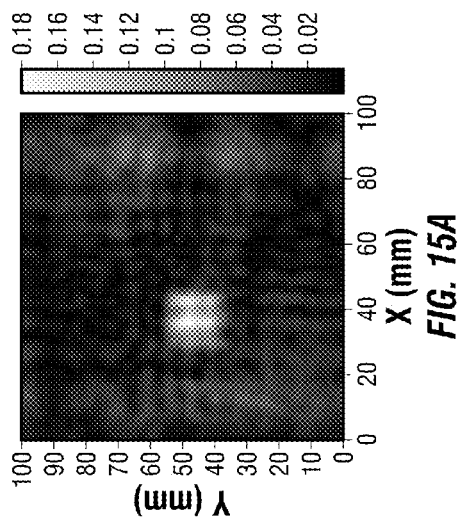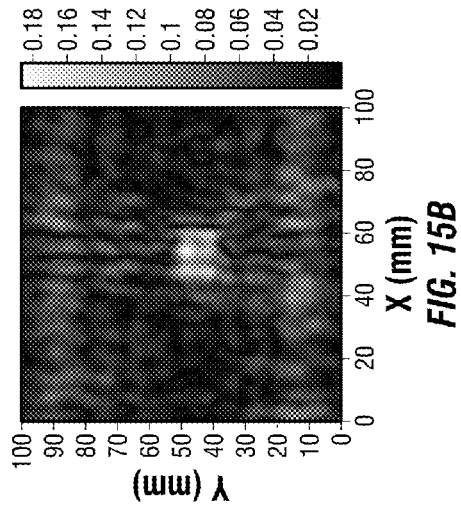

TIRE INSPECTION USING MICROWAVE IMAGING METHODOLOGIES

BACKGROUND

Tire repair and tire retreading is well known in the art. It is also well known that some level of inspection of the tires prior to repair or retreading is normally conducted to determine whether it is appropriate to perform the operation. While in some instances inspection may include simple visual inspection, it is often important in the case of retreading to determine the condition of internal components of the tire including, for example, voids in the tire's sidewall that may have developed as a result of delamination of the tire materials.

Such inspections have been performed using x-ray analysis based upon visual or shearographic image inspection. Frequently shearographic image inspection is actually followed by x-ray inspection to determine if an identified abnormality is related to the casing wires. Shearographic images can be qualitative in their result and x-ray usage can be subject to regulatory restrictions. Such method can also be time consuming and the required equipment is expensive to own and operate. It would be advantageous, therefore, to develop apparatus and methodologies that eliminate the need for some of these expensive and time-consuming methods. It would also be advantageous to have an apparatus and methodology that produce more detail results and with a more quantitative assessment of the internal state of the tire.

Microwave imaging methodologies are one alternative that may solve the problem stated above. Microwave and millimeter-wave signals span the frequency range of ~300 MHz to 30 GHz and 30 GHz to 300 GHz, corresponding to the wavelengths of 1,000 mm to 10 mm and 10 mm to 1 mm, respectively, Signals at these frequencies can easily penetrate inside dielectric materials and composites and interact with their inner structures. For material characterization purposes, this interaction may take the form of reflections from undesired flaw boundaries, such as disbands, delaminations, and voids. The relatively small wavelengths and wide bandwidths associated with these signals enable the production of high spatial-resolution images of materials and structures. The availability of a wide array of probes and transducers coupled with signal polarization diversity and coherence (magnitude and phase information) properties can be effectively manipulated for enhancing measurement accuracy and robustness. Optimization of measurement techniques and parameters can also significantly improve interior flaw detection capability.

SUMMARY OF THE INVENTION

A method of inspection of a tire using microwave imaging has been developed. The method comprises the steps of selecting a plurality of regions from within a tire to be imaged; determining the dielectric properties of the tire components in each of the selected regions in a plurality of frequency bands; selecting a specific location on a tire to be imaged; providing a scanning platform for microwave imaging of the tire; imaging the selected location on a tire using microwave imaging at a plurality of microwave scanning frequencies and at a selected microwave polarization to obtain images of the internal state of the sample; and filtering the images to remove the effects of curvature of the selected location on the tire.

The step of determining the dielectric properties may further comprise preparing a plurality of samples representing the selected regions from within the tire and measuring the dielectric properties of each of the samples in a plurality of frequency bands, for example, in the S-band, the X-band, and the Ku-band.

The imaging step comprises measuring a calibrated wideband reflection coefficient on a uniform two-dimensional grid in a plurality of frequencies, for example in the K-band, the Ka-band, and the Q-band. The imaging step comprises selecting one or both of parallel or perpendicular polarization as referenced to the orientation direction of an internal reinforcement in the tire. In particular, when the selected location on the tire to be imaged contains stranded reinforcements, the selected polarization is parallel to the longitudinal direction of the reinforcements. The imaging step may be performed prior to repair or retreading of the tire.

BRIEF DESCRIPTION OF THE DRAWINGS

A full and enabling disclosure of the present invention, including the best mode thereof, directed to one of ordinary skill in the art, is set forth in the specification, which makes reference to the appended Figures, in which:

FIGS. 7A and 7B: Ka-band scan of the "flat" rubber sample from the top-side showing insert 1 using: (a) parallel and (b) perpendicular polarization.

FIGS. 8A and 8B: Ka-band scan of the "flat" rubber sample from the bottom-side showing inserts 5 and 6 using: (a) parallel and (b) perpendicular polarization.

FIGS. 14A and 14B: K-band images of 20 mm-void in the tire carcass-rubber-aluminum plate test sample at using: (a) parallel and (b) perpendicular polarization.

FIGS. 15A and 15B: Ka-band images of 20 mm-void in the tire carcass-rubber-aluminum plate test sample using: (a) parallel and (b) perpendicular polarization.

DETAILED DESCRIPTION

Figure 1:
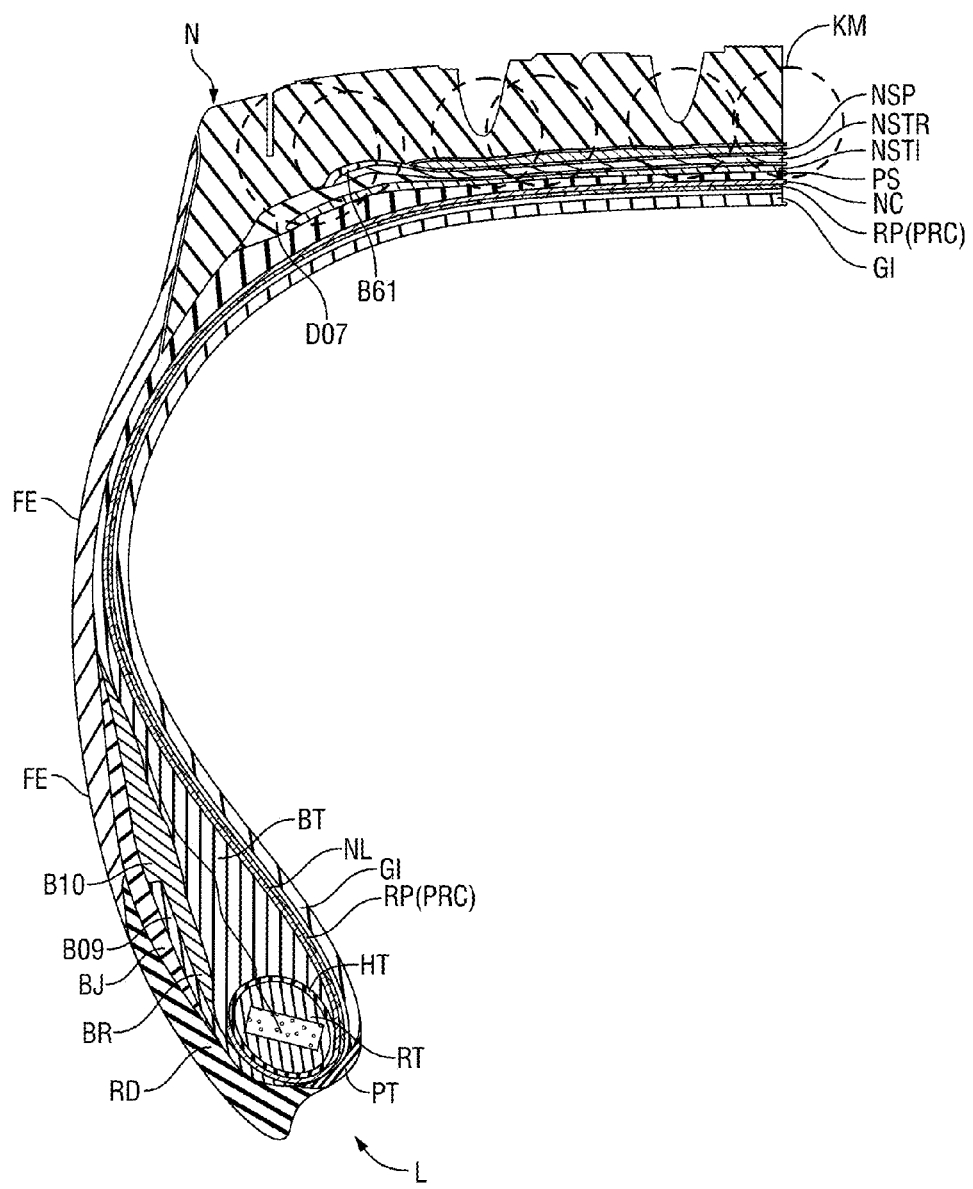
FIG. 1: A schematic of tire indicating the location of various rubber types.

The present invention provides an improved methodology for inspection of tires, especially prior to retreading or repair. The present invention is of particular interest for the inspection of heavy truck tires prior to repair or retreading. Microwave and millimeter-wave signals span the frequency range of ~300 MHz to 30 GHz and 30 GHz to 300 GHz, corresponding to the wavelengths of 1,000 mm to 10 mm and 10 mm to 1 mm, respectively. Signals at these frequencies can easily penetrate inside dielectric materials and composites and interact with their inner structures. For material characterization purposes, this interaction may take the form of reflections from undesired flaw boundaries, such as disbands, delaminations, and voids, produced during the manufacturing process or as a result of in-service stresses. The relatively small wavelengths and wide bandwidths associated with these signals enable the production of high spatial-resolution images of materials and structures. The availability of a wide array of probes and transducers coupled with signal polarization diversity and coherence (magnitude and phase information) properties can be effectively manipulated for enhancing measurement accuracy and robustness. Optimization of measurement techniques and parameters can also significantly improve interior flaw detection capability.

To optimize an imaging and detection method for a specific structure such as a tire, it is necessary to have a priori knowledge about its structural features (e.g., presence, location, and direction of steel belts, dielectric properties of rubber used, etc.). Microwave signals cannot penetrate through solid electrically conducting (e.g., metallic) structures. However, by optimizing the polarization of the microwave signal, it is possible to minimize reflections from certain metallic structures such as unidirectional conducting wire mesh. As used herein, the term parallel polarization means that the electric field vector is parallel to the longitudinal direction of any reinforcements or other structure within the tire. Likewise, the term perpendicular polarization means that the electric field vector is perpendicular to the longitudinal direction of any reinforcements or other structure within the tire. Furthermore, the dielectric properties of the various rubber types inside the tire will affect the resolution and penetration depth of the signal. The relative (to free-space) dielectric constant of a material is a complex quantity ($\epsilon_r = \epsilon_r' + j\epsilon_r''$) where the real part ($\epsilon_r'$) is the relative permittivity and represents the ability of the material to store electromagnetic energy and the imaginary part ($\epsilon_r''$) is the relative loss factor indicating the ability of the material to absorb electromagnetic energy. From an imaging point of view, higher permittivity results in shorter wavelength and consequently higher resolution. Furthermore, higher permittivity contrast between a flaw (i.e., air void) and the surrounding environment (i.e., rubber) results in more scattering and subsequently enhanced flaw detection. Higher loss factor, on the other hand, is not desirable since it limits the penetration depth of the electromagnetic signal inside the material reducing flaw detection capability.

Dielectric Characterization

From the foregoing paragraph, it is seen that a knowledge of the dielectric properties of the materials to be imaged in the selected regions of the tire will allow the choices for the microwave imaging to be optimized. The dielectric properties of the materials may be known a priori by prior experimental determination or by published sources in the technical literature. For the tire analysis discussed herein, a total of 26 rubber samples, two of each type for a total of 13 different materials chosen from selected locations within a tire, were prepared. The dielectric constant of these samples was measured in three frequency bands, as shown in Table 1. For each frequency band, at least two rectangular cuts of each material, with dimensions corresponding to respective rectangular waveguide sizes, were prepared to fit tightly inside of waveguide sample-holders. The measurements were conducted using the two-port completely filled rectangular waveguide technique.

The results of these tests show that all the rubber samples with the exception of one, have a relatively high permittivity which is on average around $\epsilon_r' = 9$. The loss factor ($\epsilon_r''$) of these rubber samples exhibited large variations from being low loss to being lossy. The loss factor decreased at higher frequencies. This trend is encouraging from imaging perspective, since higher frequencies provide for higher image resolution as well. FIG. 1 is a schematic view of a heavy truck tire in the meridian plane of the tire showing some of the regions of interest for inspection. Once the dielectric properties of the various regions of the tire are known, then the imaging algorithm may be optimized for each specific region.

TABLE 1

| Waveguide frequency bands used for dielectric characterization of rubber. | | | |
|---|---|---|---|
| Frequency Band | Frequency Range (GHz) | Waveguide Standard | Waveguide Size (in) |
| S | 2.6-3.95 | WR-284 | 2.840 × 1.340 |
| X | 8.2-12.4 | WR-90 | 0.900 × 0.400 |
| Ku | 12.4-18 | WR-62 | 0.622 × 0.311 |

Imaging of "Flat" Sample

Figures 2A, 2B:
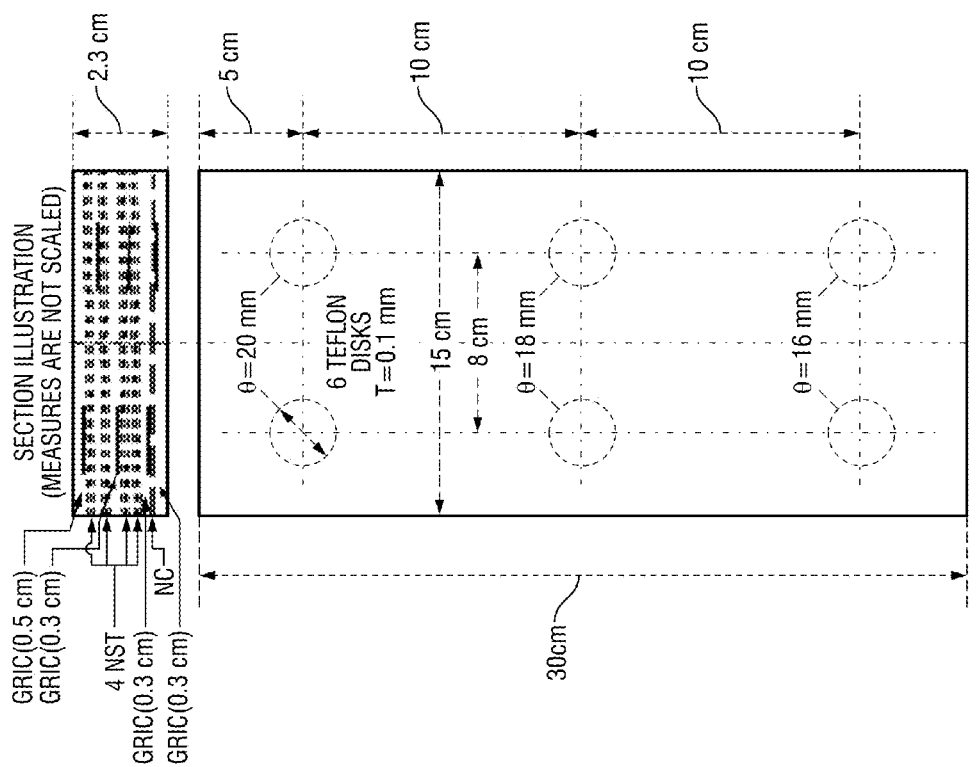
FIG. 2A and FIG. 2B: A respective schematic and a picture of the "flat" rubber sample with Teflon inserts.

A relatively flat multilayer rubber sample, as shown in FIGS. 2 and 2A, was prepared to optimize and establish the capabilities of the imaging techniques for tires. The sample, although "flat," had a reasonably noticeable curvature to it, which can present more problems at relatively higher frequencies. This sample further comprises various rubber and metallic mesh layers. Six thin Teflon inserts were embedded at various layer interfaces to mimic voids that may occur in a tire. Microwave signals do not penetrate through the multi-directional metallic wire mesh (e.g., NST), therefore it was not expected to detect inserts 2, 3, and 4. Insert 1 was expected be detected from the topside, and inserts 6 and 5 from the bottom-side. Insert 5 is behind a unidirectional metallic wire fabric (tire carcass) and was not expected be detected, unless only appropriate signal polarization would aid in potentially detecting it (i.e., polarization vector orthogonal to the direction of wires).

This sample was imaged using a 30-SAR imaging method [3]-[5]. 30-SAR imaging involves measuring calibrated wide-band reflection coefficient data on a uniform two-dimensional grid (i.e., raster scan). This is achieved by raster scanning an imaging probe (open-ended rectangular waveguide probe) over the grid using a computer-controlled mechanical 2-dimensional positioning system. Imaging was performed at three frequency bands, namely; K-band (18-26.5 GHz), Ka-band (26.5-40 GHz), and Q-band (33-50 GHz). Imaging at K-band was conducted using a commercial HP851 OC vector network analyzer; at Ka-band, a custom-made reflectometer was used; and at Q-band, a custom-made vector reflectometer [6] was used. The Q-band system only covered the frequency range of 35-45 GHz. Some of the flaw (void) indications in the microwave images in this report are relatively faint and may not clearly be visible in print. These images are best displaced on LCD screens.

Figure 3A:
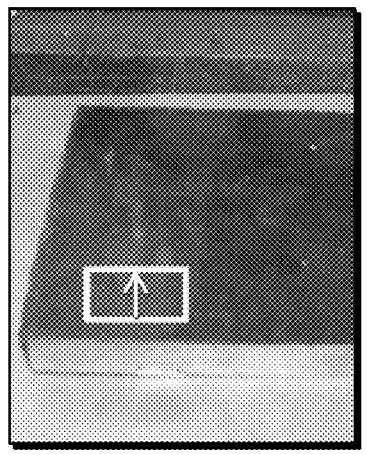
FIGS. 3A and 3B: A respective picture and K-band scan of the "flat" rubber sample focused at the insert location, with signal polarization perpendicular to the tire carcass wire direction.
Figure 3B:
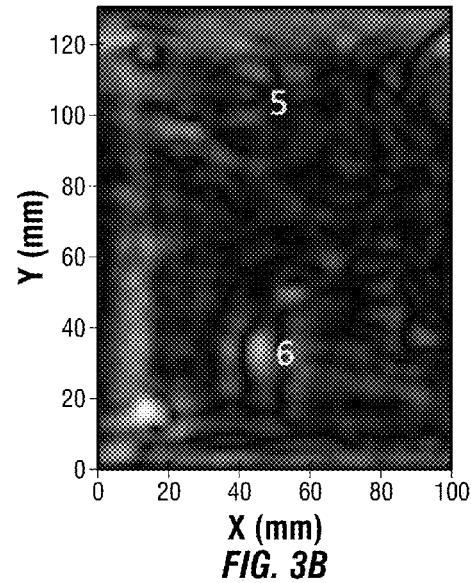
Figure 4A:
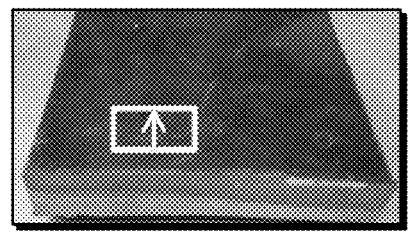
FIGS. 4A, 4B and C: Picture of the "flat" rubber sample focused at the insert locations and K-band scans of the "flat" rubber sample with signal polarization parallel to the tire carcass wire direction (left image focused at insert 5 and right image focused at insert 6).
Figure 4B:
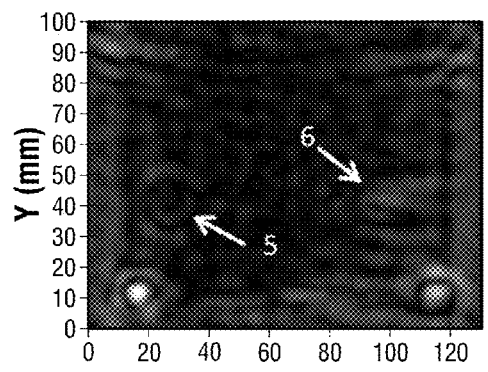
Figure 4C:
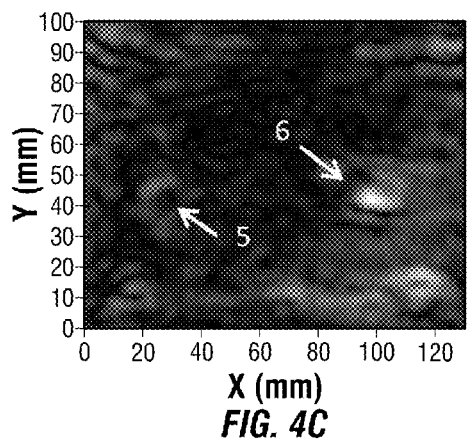
Figure 5A:
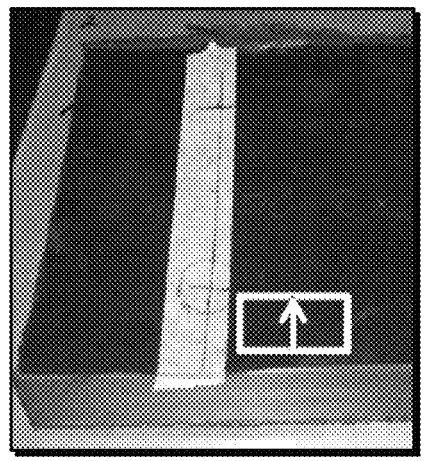
FIGS. 5A and 5B: A respective picture and K-band scan of the "flat" rubber sample with perpendicular to tire carcass polarization from the top-side focused at insert 1 location.
Figure 5B:
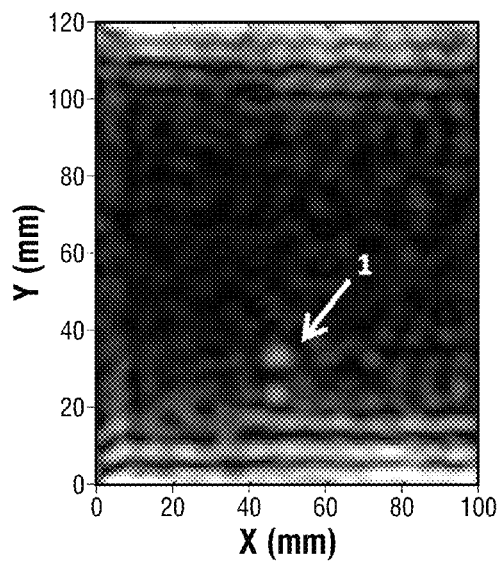
Figure 6A:
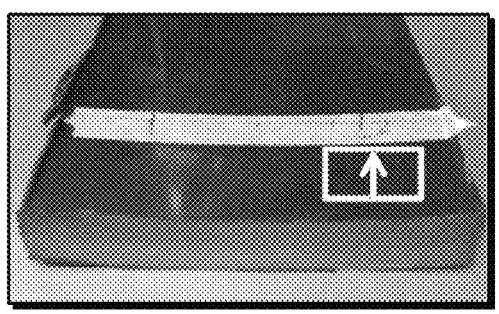
FIGS. 6A and 6B: Picture and K-band scan of the "flat" rubber sample parallel to tire carcass polarization from the top-side focused at insert 1 location.
Figure 6B:
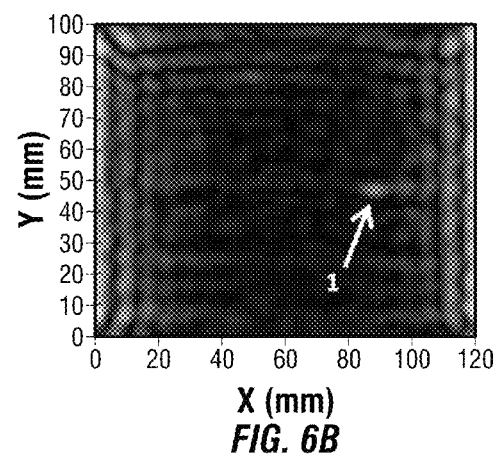

FIGS. 3 and 3A show the picture of the sample and its corresponding K-band image focused (from the bottom-side) at the location of the Teflon inserts. The polarization of the signal, as indicated by the red arrow on the picture, was perpendicular to the tire carcass wires. The white rectangle indicates the aperture of the open-ended waveguide probe. This image shows indications of Teflon inserts 5 and 6. Since the sample was not exactly flat and was somewhat curved, insert images may be masked by the effect of this curvature. Consequently, prior to image production, the measured reflection coefficient data was passed through a spatial high-pass filter to help remove the effect of the curvature as much as possible. The curvature and the subsequent filtering process affect the shape of the Teflon insert indications for two possible reasons. First, due to small bandwidth (inadequate range resolution), the indication of the Teflon insert and the indication of the curve are indistinguishable from each other. Second, spatial filtering removes parts of the signal belonging to the indication since they are contained in similar regions in the spatial spectral domain. FIGS. 4, 4A and 4B show similar images obtained by using a signal polarization parallel to the tire carcass wires. Once again, the data was filtered to remove (as much as possible) the effect of surface curvature. The two resulting images (from left to right) are focused at the location of inserts 5 and 6, respectively. At K-band, the range resolution is not adequate to focus on each of these inserts individually. However, due to the strong interferences and multiple reflections within the sample, the indications of the inserts could be made clearer by changing the focus distance slightly. It must be noted that, with SAR imaging, focusing the image is performed numerically. In other words, there is no need to re-measure the data if one wishes to focus at a different depth inside the sample. FIGS. 5A and 5B, along with FIGS. 6A and 6B, show images obtained by scanning the top-side of the sample with perpendicular and parallel (to tire carcass wire direction) polarizations, respectively. Strong scattering from the sample edges causes interference patterns represented by parallel lines on the sides of the images. The effect of sample curvature was removed by filtering with a spatial 2-D high-pass filter, as before, An indication of Teflon insert 1 is seen as a bright spot. This indication does not represent the circular shape of the insert and we believe the distortion is due to the effects of curvature and filtering. It must be noted that without filtering, the indications could not be seen.

The K-band imaging results showed the limitations of this band for properly and accurately imaging insert shape, due to its relatively low frequency range (for imaging these samples). Next, a custom-made Ka-band system was used to image this rubber sample. Ka-band provides 13.5 GHz of bandwidth centered around 33.25 GHz, which translates to a range resolution (depth) of ~3.7 mm inside rubber with $\epsilon_r = 9$. FIGS. 7A and 7B show a Ka-band image of the rubber sample from the top-side at two polarizations. These Figs. clearly show the circular shape of insert 1. The effect of the sample curvature can also be observed in these images. The sample edges scatter strongly and create clutter, in the form of parallel bright and dark lines in the image. Furthermore, due to non-sufficient coverage of the scan area and aliasing effect in the SAR algorithm, the indication of the edge repeatedly appears throughout the image as parallel lines. This effect can be removed by non-uniform scanning or other advanced signal processing techniques. FIGS. 8A and 8B show the Ka-band images from the bottom-side using two orthogonal polarizations. In these images, both insert 6 and insert 5 (through the tire carcass layer) are imaged, The effect of the sample curvature and edges are also observed.

Figure 9B:
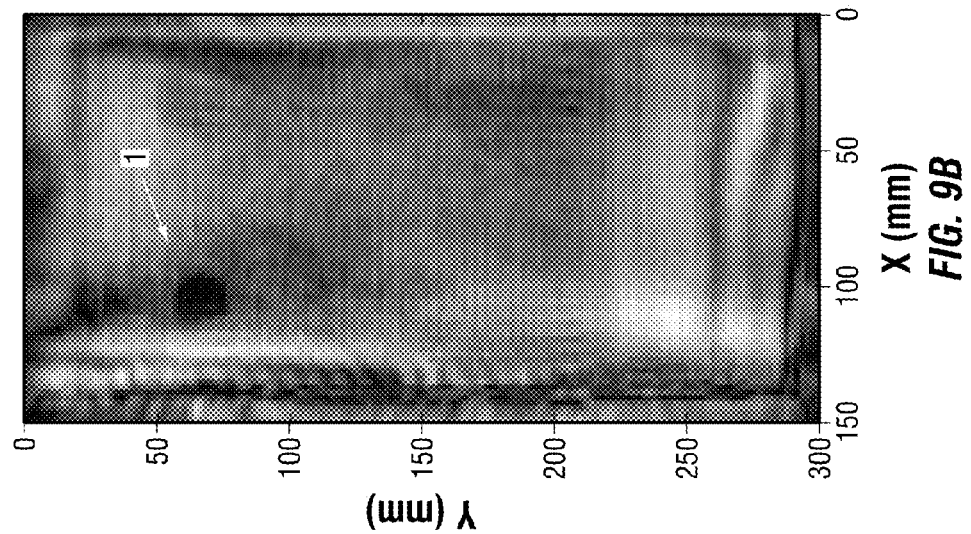
FIGS. 9A and 9B: Q-band scan of the "flat" rubber sample from the top-side showing insert 1 using: (a) parallel and (b) perpendicular polarization.
Figure 9A:
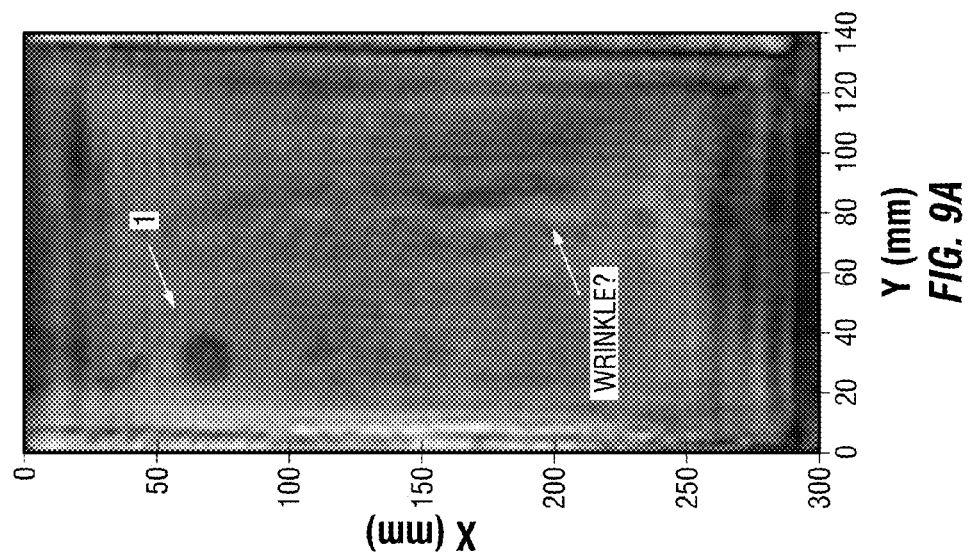
Figure 10B:
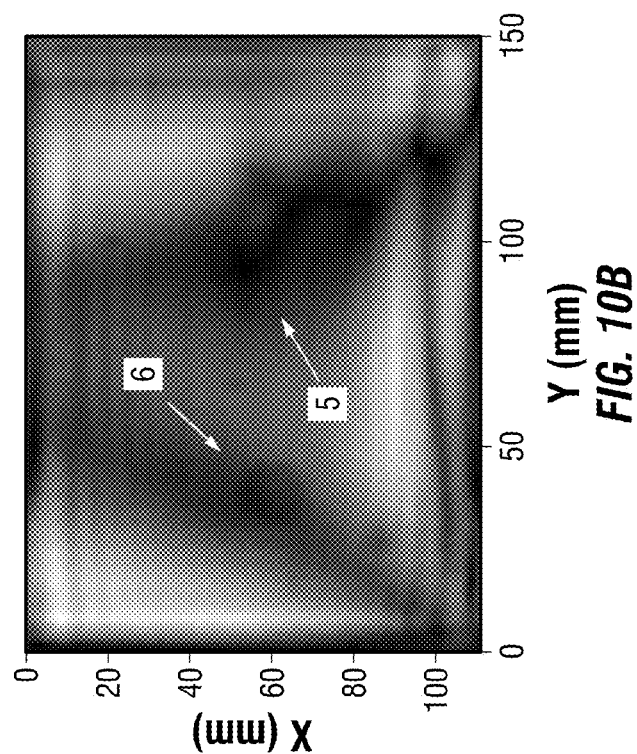
FIGS. 10A and 10B: Q-band scan from the bottom-side showing inserts 5 and 6 using: (a) parallel and .(b) perpendicular polarization.
Figure 10A:
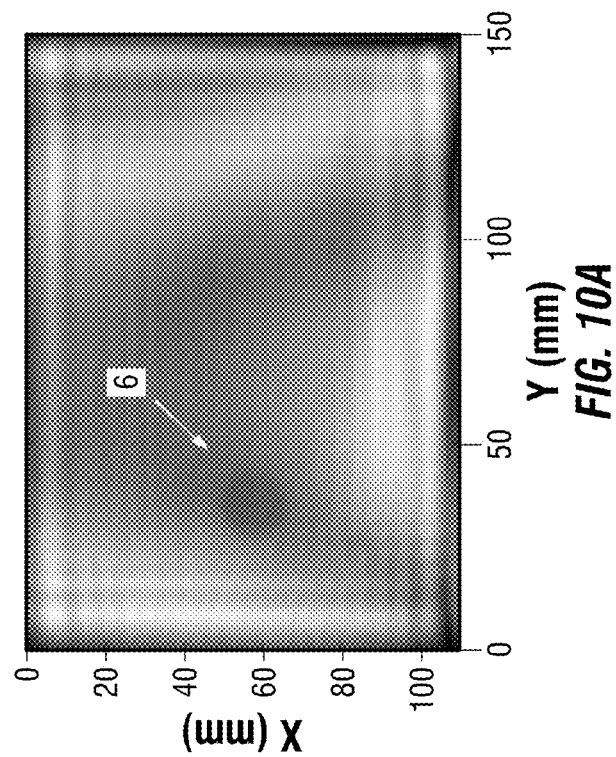

Finally, the Q-band system was used to image this sample. Q-band provides for higher resolution due to the higher frequencies in this band. FIGS. 9A and 9B show two images at two polarizations from the top-side of the sample. As expected insert 1 is clearly visible, along with other features in the sample such as a possible wrinkle in the multi-directional NST metal mesh along the length of the sample. FIGS. 10A and 10B show the images obtained from the bottom-side, Insert 5 is barely detected at perpendicular polarization due to the adverse effect of the sample curvature, while it is not detected at parallel polarization.

Considering the above imaging results, although it was expected that we should be able to somewhat detect/see insert 5 through the tire carcass layer using perpendicular polarization, it was not expected that we would also see the insert though the tire carcass layer using parallel polarization. This effect was further investigated, and will be discussed in detail in the next section.

Investigation of Imaging Through the Tire Carcass Fabric

Figure 11A:
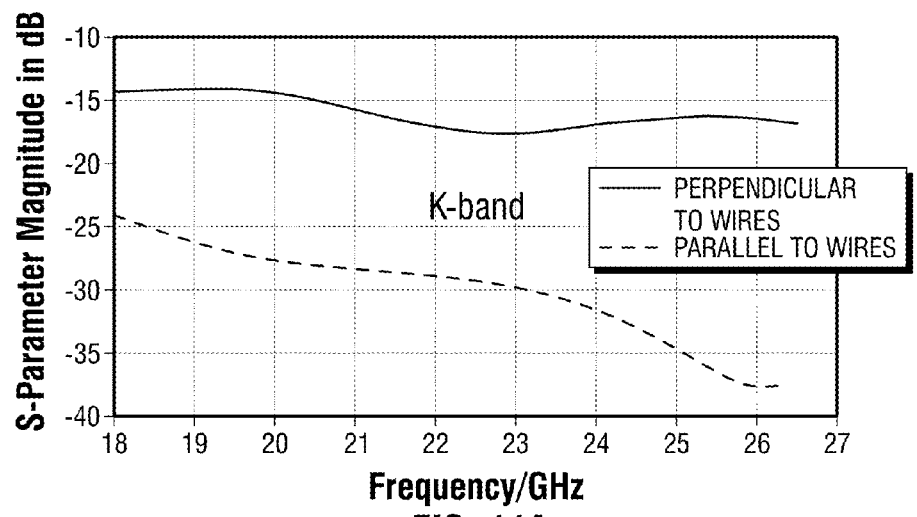
FIGS. 11A and 11B: Simulated transmission through unidirectional metallic mesh at K-band and Ka-band.
Figure 11B:
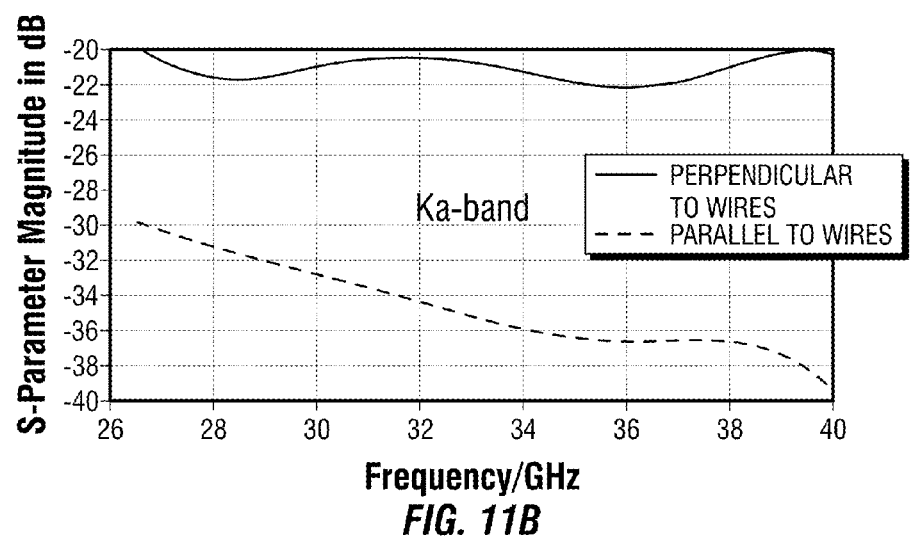
Figure 12A:
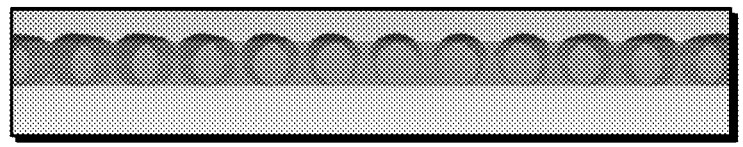
FIGS. 12A and 12B: Simulated surface current on unidirectional metallic mesh at 40 GHz perpendicular to wires and parallel to wires, respectively.
Figure 12B:
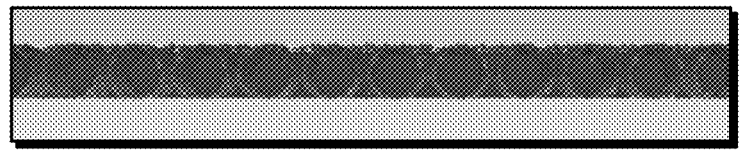

When imaging the "flat" rubber sample, an unexpected phenomenon occurred which was not completely consistent with our understanding of imaging through unidirectional metallic wire mesh, such as the tire carcass layer. To this end, an experimental followed by a numerical simulation study were performed in order to better understand this phenomenon, and, perhaps to provide a better technical understanding of this result. FIGS. 11A and 11B show the amplitude of power transmitted through a simulated fire carcass layer at K-band and Ka-band. The wires in the tire carcass wire mesh were simulated as one solid conductor (as opposed to being manufactured from several thin stranded and twisted wires). As expected, in both frequency bands, there is at least a 10 dB higher signal transmission through the mesh at perpendicular (to the wire direction) polarization compared to when using parallel polarization. FIGS. 12A and 12B show surface current generated by an incident plane-wave on the unidirectional metallic mesh with parallel and perpendicular polarizations. The results show a cross-sectional view of the solid conductors. The plane-wave is incident on the wires from the top. When the incident signal polarization is parallel to the wires, the surface current is primarily confined to the top surface of the conductors and almost no current flows on the back-side of the wires, causing nearly total reflection of the signal. On the other hand, when the signal polarization is perpendicular to the wires, the surface current wraps around the wires and a small portion of signal goes through the wire mesh. These findings do not fully justify the images obtained from the "flat" rubber sample with Teflon inserts. In those images, some images at parallel polarization were more indicative of the insert below the tire carcass wire mesh (insert 5) than the perpendicular polarization.

Figure 13A:
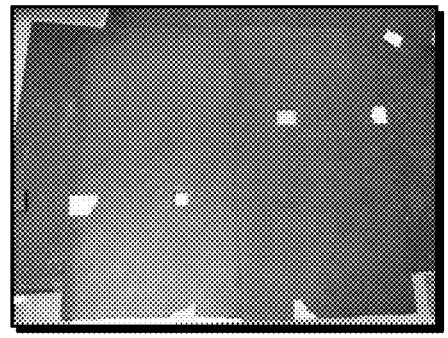
FIGS. 13A and 13B: Experimental sample (tire carcass-rubber-aluminum plate) for testing imaging through tire carcass with (a) rubber placed on aluminum plate with square voids cut-out and (b) sample covered by tire carcass mesh.
Figure 13B:
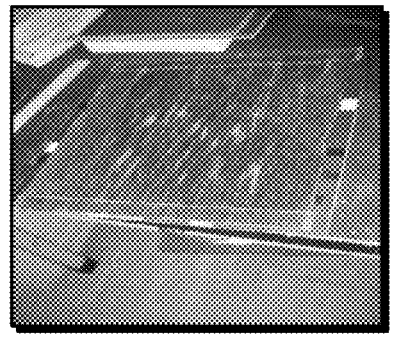
Figure 16A:
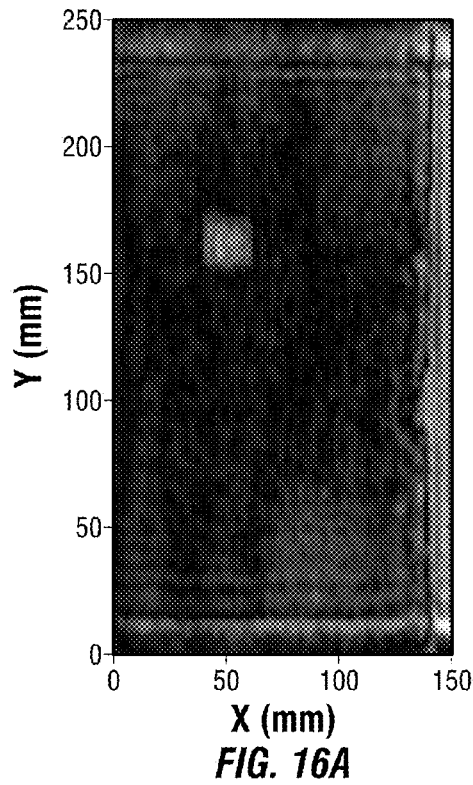
FIGS. 16A and 16B: Q-band images of the 20 mm-void in the tire carcass-rubber aluminum plate test sample using: (a) parallel and (b) perpendicular polarization.
Figure 16B:
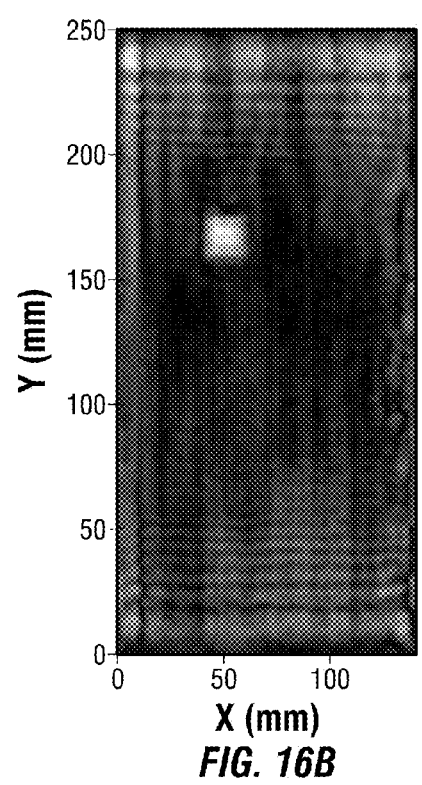
Figure 17A:
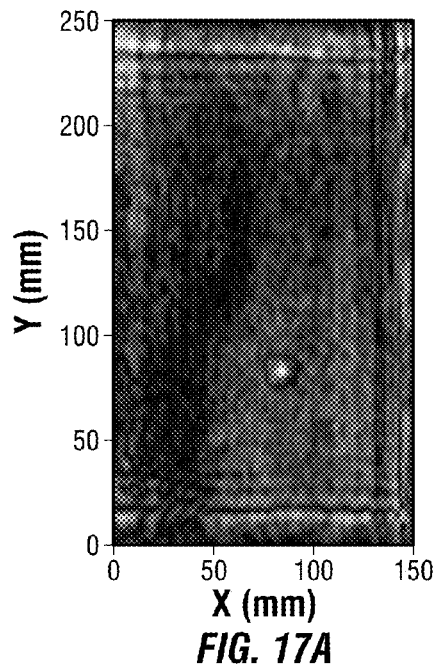
FIGS. 17A and 17B: Q-band images of the 15 mm-void in the tire carcass-rubber-aluminum plate test sample using: (a) parallel and (b) perpendicular polarization.
Figure 17B:
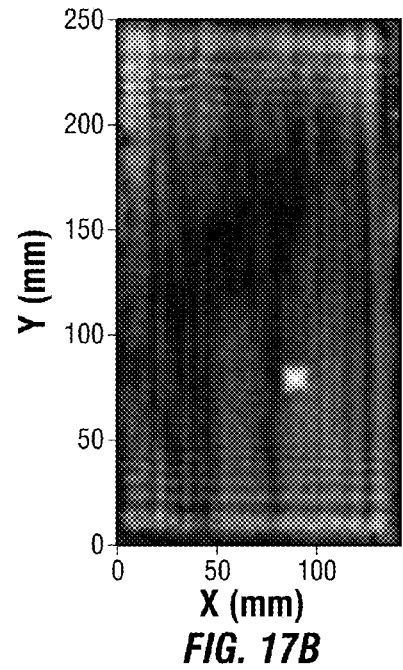

To further investigate this issue experimentally, a few tire carcass meshes (i.e., fabrics) were obtained from the sponsor. A 5 mm-thick rubber was placed on a 12"×12" aluminum plate. Two square-shaped areas with side dimensions of 15 mm and 20 mm were cut out of the rubber sheet (representing thin voids), as shown in FIGS. 13A and 13B. Subsequently, the tire carcass mesh was placed on top of this rubber sheet. The composite fire carcass-rubber-aluminum plate sample was constructed in this way to mimic reasonably the fire carcass-rubber-NST configuration in the "flat" rubber sample with Teflon inserts, as imaged earlier. This sample was imaged using the K-band, Ka-band, and Q-band systems. At K-band using both polarizations the 20 mm-void was detected, as shown in FIGS. 14A and 14B. The image using the parallel polarization is somewhat distorted and relatively faint compared to the perpendicular polarization case, which corroborates the original understanding of imaging through unidirectional conducting wires. Using higher frequencies at Ka-band, resulted in images from both polarization for the 20 mm-void, as shown in FIGS. 15A and 15B. Furthermore, at parallel polarization, the indication of the void more accurately resembles the 20 mm-void and the image shows relatively minimal clutter compared to the perpendicular polarization case. Using even higher frequencies, at Q-band, resulted in much better indications of the voids at parallel polarization, as shown in FIGS. 16A and 16B. Additionally, smaller voids (15 mm square) are better detected with parallel polarization compared to the perpendicular polarization, as shown in FIGS. 17A and 17B.

These results are contradictory to our previous understanding of imaging through unidirectional conducting fiber mesh. This phenomenon can be explained by the fact that some of the currents flowing on the wires travel to the back-side of the wires. When this current interacts with the voids, they disturb the currents flowing on the wire mesh surface, and thus affect the properties of the reflected waves, which is consequently registered in the imaging results. We also suspect that the higher frequencies and the fact that the tire carcass wires are stranded and twisted help to increase the amount of currents flowing to the back surface of the wires. It is also possible that the slight bulging caused by embedding the inserts is being detected, which would be better detected and imaged at higher frequencies.

Figure 18A:
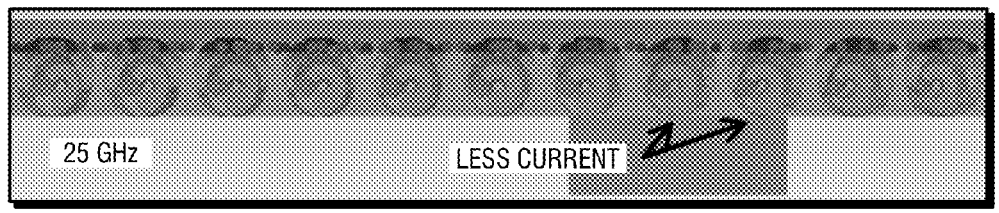
FIGS. 18A and 18B: Simulated surface current on solid wires at two frequencies of 25 GHz and 40 GHz, respectively.
Figure 18B:
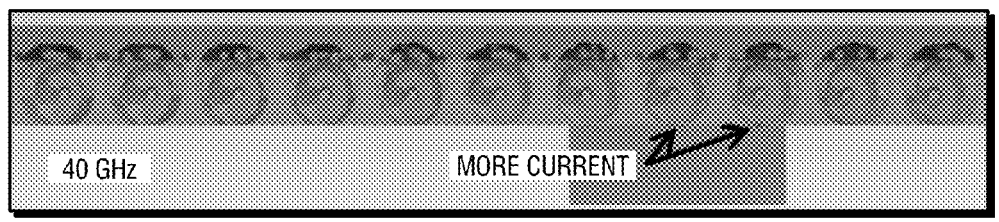

FIGS. 18A and 18B show the simulated surface currents on solid conductors due to a plane wave at 25 GHz and 40 GHz, respectively. The wire diameter is set to 0.7 mm and the separation between wires is set to 0.3 mm. These wires are incased in a rubber sheet with permittivity with $\in_r=9$. These Fig. show that at higher frequency, more current flows to the back of the conductor that helps in detecting voids behind the the carcass layer. Considering at 40 GHz and rubber permittivity of $\in_r=9$, the wavelength is 2.5 mm, thus the separation between the wires is quite large for this sheet to be considered a solid conducting sheet and not being able to image through it.

Figure 19A:
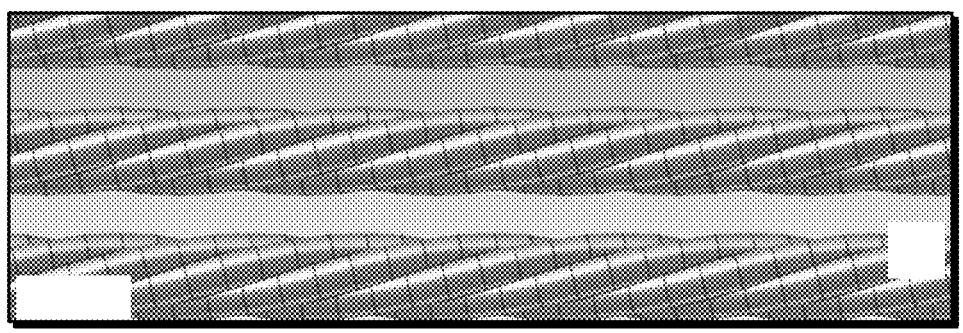
FIGS. 19A and 19B: Simulated tire carcass layer as stranded and twisted wires, respectively.
Figure 19B:
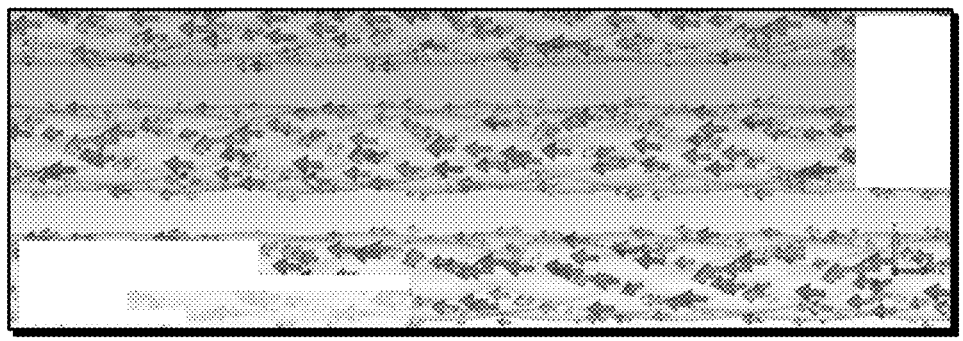
Figure 20A:
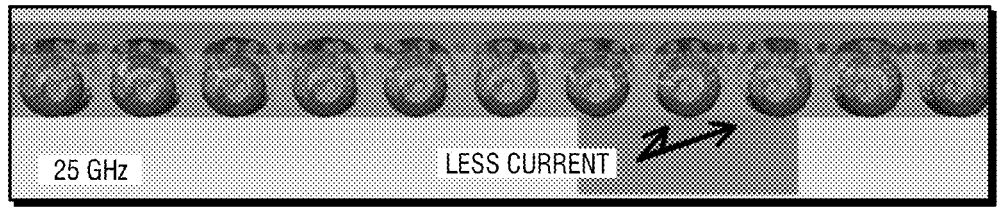
FIGS. 20A and 20B: Simulated surface current on twisted stranded wires at two frequencies of 25 GHz and 40 GHz, respectively.
Figure 20B:
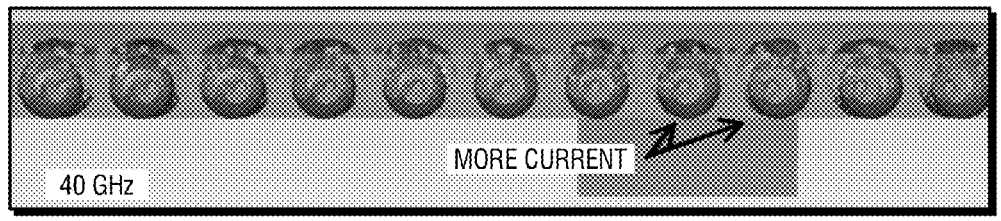
Figure 21A:
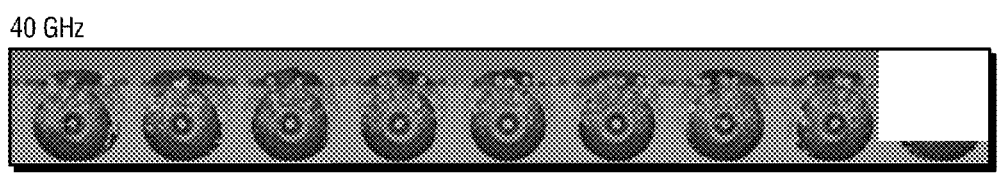
FIGS. 21A and 21B: Effect of stranded wire twist angle on current distribution, respectively.
Figure 21B:
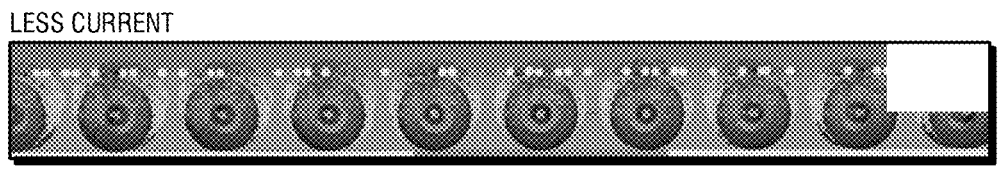

FIGS. 19A and 19B show simulated tire carcass layer as a twisted stranded wire mesh. To reduce computational resources, only 4 strands were used here to create/represent an individual wire. These strands were wrapped around a solid core. The wire diameter and separation were as those before. As shown in FIGS. 19A and 19B, while most of the current flows along the wire, some current follows along the twist. FIGS. 20A and 20B show cross-sectional views of the currents flowing on the twisted stranded wires at 25 GHz and 40 GHz, respectively. The results in FIGS. 20A and 20B are similar to those in FIGS. 18A and 18B and no substantial change is noticed due to the twisted wires compared to the solid wires. FIGS. 21A and 21B show the effect of the twist angle on the amount of current flowing to the back of the wires. The results indicate that higher twist angle leads to more currents flowing to the back of the wires. Overall, it appears that a combination of the high frequencies and the twist of the strands may be the cause of this phenomenon (i.e., seeing through the wires with parallel polarization). Furthermore, the combination of the tire carcass layer and the NST layer beneath it can create a resonant condition (e.g., cavity) that can further enhance detection. The effect of bulging due to the inserts may also contribute to the ability to image variations at the location of an insert. These results are preliminary, and further investigation is needed to understand fully this phenomenon. To do so, additional simulation and experimental verification is required to optimize the frequency and imaging technique through the tire carcass layer. However, it appears that when the selected location on the tire to be imaged contains stranded reinforcements, such as the cables and cords commonly used in tires, then it is advantageous to select a polarization parallel to the longitudinal direction of the reinforcements.

A method of tire inspection using microwave imaging was developed and evaluated using flat rubber samples with Teflon inserts. Electromagnetically, the Teflon inserts produce lower contrast to rubber compared to air voids. Yet, the contrast was sufficient for detecting the Teflon inserts. The "flat" rubber sample with Teflon inserts showed that higher frequency at Ka- or Q-bands produce better images. The images also showed the adverse effect of sample curvature. The method produced the unexpected result that it is possible to obtain images of voids under the tire carcass layer using parallel polarization. Since this was unexpected, a comprehensive experimental and theoretical (simulation based) study followed and showed that a combination of higher frequencies, separation between the wires, and stranded twisted wires, and last but not least the surrounding high permittivity rubber made possible to obtain clear images of voids behind tire carcass fabric with high accuracy.

While the present subject matter has been described in detail with respect to specific exemplary embodiments and methods thereof, it will be appreciated that those skilled in the art, upon attaining an understanding of the foregoing, may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

The invention claimed is:

1. A method of inspection of a tire using microwave imaging comprising the steps of:
    selecting a plurality of regions from within a tire to be imaged;

determining the dielectric properties of the tire components in each of the selected regions in a plurality of frequency bands;

selecting a specific location on a tire to be imaged;

providing a scanning platform for microwave imaging of the tire;

imaging the selected location on a tire using microwave imaging at a plurality of microwave scanning frequencies and at a selected microwave polarization to obtain images of the internal state of the sample; and filtering the images to remove the effects of curvature of the selected location on the tire.

2. The method of claim 1 wherein the step of determining the dielectric properties further comprises preparing a plurality of samples representing the selected regions from within the tire and measuring the dielectric properties of each of the samples in a plurality of frequency bands.

3. The method of claim 1 wherein the measuring step comprises frequencies in the S-band, the X-band, and the Ku-band.

4. The method of claim 1 wherein the measuring step comprises a two-port, completely filled waveguide measuring technique.

5. The method of claim 1 wherein the imaging step comprises measuring a calibrated wide-band reflection coefficient on a uniform two-dimensional grid.

6. The method of claim 5 wherein the imaging step comprises scanning frequencies in the K-band, the Ka-band, and the Q-band.

7. The method of claim 1 wherein the imaging step comprises selecting one or both of parallel or perpendicular polarization as referenced to the orientation direction an internal reinforcement in the tire.

8. The method of claim 7 wherein the selected location on the tire to be imaged contains stranded reinforcements and the selected polarization is parallel to the longitudinal direction of the reinforcements.

9. The method of claim 1 wherein the filtering step is performed with a spatial 2-D high-pass filter.

10. The method of claim 1 wherein the imaging step comprises scanning frequencies in the Q-band.

11. The method of claim 1 wherein the imaging step is performed prior to repair or retreading of the tire.

12. The method of claim 11 wherein the filtering step is performed prior to repair or retreading of the tire.

13. The method of claim 1 wherein the tire is a heavy truck tire.

* * * * *